US009226786B2

(12) United States Patent
Tran et al.

(10) Patent No.: US 9,226,786 B2
(45) Date of Patent: Jan. 5, 2016

(54) MEDICAL DEVICES FOR CLEARING A SURGICAL SITE

(75) Inventors: Nathaniel Tran, Apple Valley, MN (US); Douglas E. Ott, Macon, GA (US)

(73) Assignee: LEXION MEDICAL LLC, St. Paul, MN (US)

( * ) Notice: Subject to any disclaimer, the term of this patent is extended or adjusted under 35 U.S.C. 154(b) by 277 days.

(21) Appl. No.: 13/385,364

(22) Filed: Feb. 15, 2012

(65) Prior Publication Data

US 2012/0245509 A1 Sep. 27, 2012

Related U.S. Application Data

(60) Provisional application No. 61/465,615, filed on Mar. 22, 2011.

(51) Int. Cl.
| | |
|---|---|
| A61B 18/00 | (2006.01) |
| A61M 13/00 | (2006.01) |
| A61B 19/00 | (2006.01) |
| A61M 16/10 | (2006.01) |
| A61M 16/16 | (2006.01) |

(52) U.S. Cl.
CPC .............. *A61B 18/00* (2013.01); *A61M 13/003* (2013.01); *A61M 16/109* (2014.02); *A61M 16/161* (2014.02); *A61B 2019/385* (2013.01); *A61B 2218/005* (2013.01); *A61M 16/1075* (2013.01); *A61M 16/16* (2013.01); *A61M 2205/3368* (2013.01)

(58) Field of Classification Search
CPC ............. A61B 18/00; A61B 2019/385; A61B 2218/005; A61M 13/004; A61M 16/161; A61M 16/109; A61M 13/003; A61M 16/105; A61M 16/1055; A61M 16/22; A61M 2202/0225; A61M 16/1075; A61M 16/16; A61M 2205/3368
USPC ................. 604/23, 24, 26, 264, 266, 268; 128/204.18
See application file for complete search history.

(56) References Cited

U.S. PATENT DOCUMENTS

| | | | | |
|---|---|---|---|---|
| 5,336,170 | A * | 8/1994 | Salerno et al. ................... | 604/24 |
| 5,545,196 | A | 8/1996 | Falk | |
| 6,156,003 | A * | 12/2000 | Suresh ............................. | 604/24 |
| 6,168,577 | B1 * | 1/2001 | Niederjohn et al. ............ | 604/23 |
| 2004/0167464 | A1 * | 8/2004 | Ireland et al. ................... | 604/66 |
| 2007/0088275 | A1 * | 4/2007 | Stearns ............... | A61B 17/3421 604/164.01 |
| 2010/0241061 | A1 * | 9/2010 | Ott ..................... | A61B 17/3474 604/26 |
| 2011/0003264 | A1 * | 1/2011 | Cohen et al. .................... | 433/32 |

FOREIGN PATENT DOCUMENTS

| | | |
|---|---|---|
| JP | 2006-061573 | 3/2006 |
| WO | WO 00-15117 A1 | 3/2000 |

* cited by examiner

*Primary Examiner* — Kami A Bosworth
*Assistant Examiner* — Brandy S Lee
(74) *Attorney, Agent, or Firm* — Jacobson & Johnson LLC

(57) ABSTRACT

An apparatus and method for clearing of a surgical site during the performance of a medical procedure where a single phase wash fluid, which has been conditioned, is directed at the surgical site to inhibit or prevent harm to the body tissue as unwanted debris is blown away from the surgical site thereby permitting a surgeon to safely perform a medical procedure without the presence of unwanted liquids or unwanted debris at the surgical site.

21 Claims, 2 Drawing Sheets

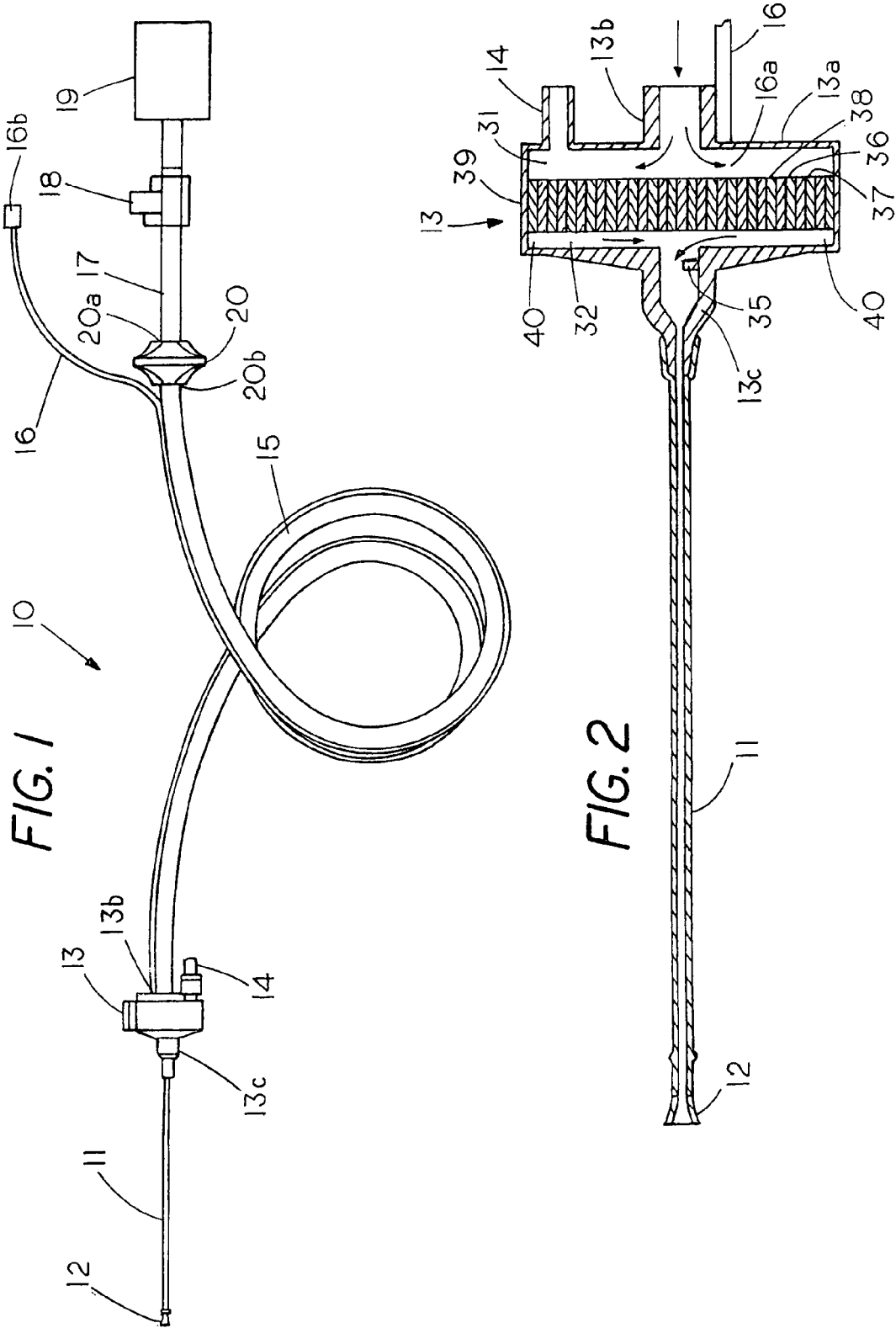

MEDICAL DEVICES FOR CLEARING A SURGICAL SITE

CROSS REFERENCE TO RELATED APPLICATIONS

This application claims priority from provisional patent application Ser. No. 61/465,615 filed Mar. 22, 2011 titled Medical Devices for Clearing a Surgical Site.

FIELD OF THE INVENTION

This invention relates generally to medical devices and, more specifically, to a medical device and a method for removing debris from a surgical site without introducing additional debris and for preserving the tissue at the surgical site.

STATEMENT REGARDING FEDERALLY SPONSORED RESEARCH OR DEVELOPMENT

None

REFERENCE TO A MICROFICHE APPENDIX

None

BACKGROUND OF THE INVENTION

The use of various types of devices for cleaning body tissue are known in the art. Some devices remove debris by suction while other devices remove debris by blowing debris away from the body tissue. An example of a surgical device that removes debris from a body tissue through suction is shown in U.S. Pat. No. 5,827,218. Other devices for cleaning body tissue include a combination of methods. An example of a device that employs multiple methods is shown in U.S. Pat. No. 5,902,264, which discloses an endoscopic surgical instruments for aspirating, irrigation and blowing gas adjacent to body tissue. These type of devices are well suited to cases where the body tissue is not adversely impacted by the cleaning action of the device. However, in some cases the body tissue is fragile and could be injured by a harsh cleaning action. In addition in some cases the body dynamics need to be considered, for example during the performance of an anastomosis, a more gentle or delicate removal of the debris proximate to a dynamic surgical site is necessary in order to preserve the integrity of the body tissue at the surgical site as blood exudes or flows from the anastomosis site.

One of such devices that have been developed for cleaning a surgical site during the performance of an anastomosis is a blower/mister, which relies on the atomization of liquid droplets. The blower/mister devices deliver a stream of pressurized gas that is intermixed with a stream of a sterile liquid to produce an intermixed stream of gas and liquid droplets, which can be used to wash debris away from the surgical site. In the blower/mister device a gas stream is directed past a liquid stream to entrain particles or droplets of the liquid in the gas stream, which results in an intermixed fluid stream of both gas and liquid droplets.

An example of a fluid entrainment device or atomization device is shown in U.S. Pat. No. 6,168,577. The fluid entrainment device contains coaxial lumens with liquid saline directed through a central lumen and a gas directed through an outer annular lumen. The gas flowing past the central stream of liquid saline entrains droplets of the saline with the gas stream. The intermixed liquid and gas stream is then directed at a surgical site to blow away debris from the surgical site.

U.S. Pat. No. 5,336,170 shows an example of another blower/mister having a fan shaped wand for blowing an intermixed gas and liquid stream onto a surgical site to blow debris away from the surgical site. One of the touted advantages of the blower/misters is that they have the ability to blow away debris from a surgical site without desiccating the tissue at the surgical site since they simultaneously deliver both a liquid and a gas to the surgical site.

Another type of blower mister, which moisturizes the fluid stream through entrainment or atomization of liquid droplets is shown in U.S. Pat. No. 6,156,003. The patent contends that the use of multiple smaller lumens each containing a liquid stream within a larger lumen containing a gas stream provides for greater efficiency in the atomization or entrainment of the liquid since the patent states smaller drops can be injected into the gas stream, which prevents liquid from dripping from his wand.

One of the more challenging tasks for a surgeon is forming an anastomosis on coronary arteries while the heart continues to beat. As the blood is pumped through the arteries it can disrupt the surgeons view of the surgical site, which further complicates the task of suturing the arteries under dynamic conditions. The suturing of an anastomosis is not only a dynamic task but also a delicate and difficult task since the ends of the arteries need to be viewed clearly in order to suture the ends of the arteries to each other. It is important that the surgeon not only have a clear view of the surgical site but he or she should have an assurance that the process of cleaning the surgical site does not harm the body tissue at the surgical site. Because of the difficult task in cleaning a dynamic surgical site without harming the tissue a tissue clearing device such as the blower/misters, which mix a gas stream and a liquid stream have been preferred. The blower/misters intermix a liquid stream and gas stream to produce a fluid stream, which is directed at the surgical site. The intermixing of the moving fluid streams occurs through a process of fluid entrainment whereby a gas stream and a liquid stream are directed along side each other. The friction between boundary layers of the two streams results in intermixing of the liquid droplets and the gas. Because of the need to enhance visualization at an anastomosis site where blood may be exuding or flowing from vessels the aforementioned devices for intermixing streams of both gas and liquid droplets, which are described in U.S. Pat. Nos. 6,168,577 and 5,336,170 have been used to blow away debris from delicate and dynamic surgical sites.

Although the aforedescribed blower/misters have been widely used to blow debris away from delicate and dynamic surgical sites they have the disadvantage that they may also introduce additional debris to the surgical site since the liquid droplets in the intermixed stream may remain at the surgical site, which has the potential to interfere with the surgeons view of the surgical site as well as affect the condition of the tissue at the surgical site. In addition, the liquid droplets, which have been entrained by the gas stream of the blower/misters, create multiple micro impacts on the tissue at the surgical site as one blows the intermixed gas and liquid stream at the surgical site. Consequently, the micro impacts of the liquid droplets have the potential to result in tissue damage at the surgical site. That is, even though the velocity of the gas stream and the velocity of the atomized liquid droplets may be the same the larger mass or momentum of the liquid droplets can generate a greater impact on the delicate tissue than the impingement of the molecules of the gas stream. Thus, while it may appear the velocity of the gas is sufficiently low so as not to harm the tissue the velocity of the liquid droplets may not be.

Another drawback with blower/misters is that oftentimes it is difficult to control the entrainment process as it often results in too much liquid saline solution or too little liquid saline solution being delivered to the surgical site.

A further disadvantage with the blower/misters is that the intermixed stream of liquid and gas leaves a residue of droplets of liquid debris at the surgical site. In addition, the liquid droplets may accumulate and coalesce at the end of the wand since the liquid droplets are always present when a two-phase stream is used to blow debris away from the surgical site.

While the use of blower/misters that intermix streams of liquid and gas are known in the art sometimes those who use the blower/misters mistakenly believe that devices that intermix the streams of liquid and gas humidify the gas, however, the coaction of fast moving streams of gas and liquid with each other actually produces entrainment or atomization of the liquid particles in the gas as opposed to humidification of the gas.

The invention described herein eliminates the problems of introducing extraneous foreign materials to the surgical site or the need for atomization of a liquid while at the same time inhibiting and preventing desiccation or injury to the tissue during the cleaning of a surgical site. The invention is well suited for cleaning and preserving tissue at delicate and dynamic surgical sites for example, an anastomosis site where blood may be exuding from a vessel during the surgical procedure. In addition the invention can eliminate the need for use of multiple fluid streams in cleaning a surgical site.

SUMMARY OF THE INVENTION

An apparatus and method for cleaning a surgical site during the performance of a medical procedure where a single phase wash gas, which has been conditioned, is directed at the surgical site to preserve the body tissue as unwanted debris is blown away from the surgical site thereby permitting a surgeon to safely perform a medical procedure without the visual hindrance of the presence of unwanted liquids or unwanted debris at the surgical site.

BRIEF DESCRIPTION OF THE DRAWINGS

FIG. 1 shows a single-phase wash gas system;

FIG. 2 shows a sectional view of the gas conditioning housing and blowpipe of the single-phase wash gas system.

DESCRIPTION OF THE PREFERRED EMBODIMENT

Figure 3:
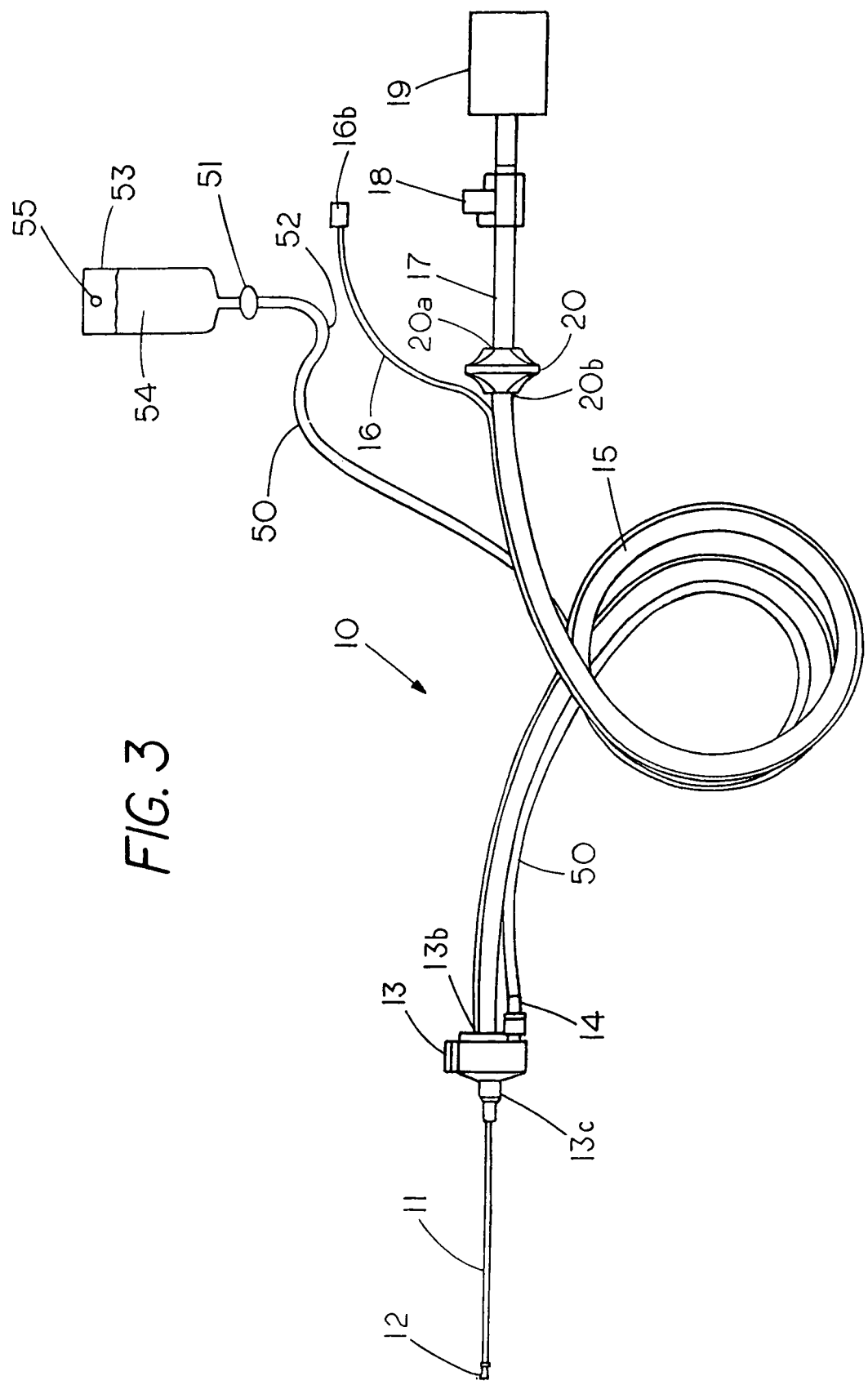
FIG. 3 shows the single-phase wash gas system connected to source of hydration fluid.

FIG. 1 shows a single-phase wash gas system 10 for removing debris from a surgical site, such as an anastomosis site, without adversely affecting the tissue at the surgical site. Wash gas system 10 comprises a source of a pressurized wash gas 19, which is in fluid communication with a manual operated pressure or flow regulator 18. Regulator 18 may be manually operated to increase or decrease the flow of wash gas therethrough. If desired a voice activated control may be employed which allows a surgeon to increase or decrease the flow of wash gas, thus leaving the surgeons hands free to perform his or her surgical task. In other cases a surgeon may vocally instruct an assistant to increase or decrease the flow and in still other cases a wash gas flow control valve may be provided at the handle of the wash gas delivery device. The wash gas used to clean a surgical site should be compatible with the body tissue as well as not generate trauma in the body tissue. An example of a suitable wash gas is carbon dioxide although other types of wash gas may be used for blowing away debris from a surgical site.

A tube 17, which may be rigid or flexible, connects the regulator 18 to an inlet 20a of gas filter 20, which removes unwanted impurities in the wash gas. A coiled flexible tubing 15 connects an outlet 20b of gas filter 20 to a central inlet port 13b on one side of gas conditioning housing 13. A second port 14 on back side 13a of housing 13 allows one to introduce a charge of a liquid such as sterile water or a sterile saline solution into the gas conditioning housing 13. An electrical cord 16 having a plug 16b thereon extends along flexible tubing 15 to provide electrical communication with a temperature sensor 36 and an electrical heater located in the gas conditioning housing 13. Located on the opposite side of gas conditioning housing 13 is an outlet 13c having an elongated tube or blowpipe 11 attached thereto with the blowpipe 11 terminating in a nozzle 12. Although blowpipe 11 may be a rigid tubing one may elect to use a flexible or bendable tubing since it allows one to manipulate the position and angle of the blow pipe 11 while using the gas conditioning housing 13 as a handle.

The conditioning of gas for use in insufflation of body cavities is well known in the art. In these cases a conditioned insufflation gas is used to inflate a body cavity so that one can perform a surgical task. Examples of devices for conditioning insufflation gas can be found in Douglas Ott et al. U.S. Pat. Nos. 5,411,474; 6,068,609 and 7,066,902 as well as pending application of U.S. application Ser. No. 12/381,978 titled GAS CONDITIONING TROCARS filed Mar. 18, 2009 which is hereby incorporated by reference.

An example of gas conditioning housing 13 for use in the present invention, is shown in cross section in FIG. 2. The gas conditioning housing 13 includes a heater assembly 37 for heating the wash gas and the sterile liquid in housing 13. While a saline solution may be used as a conditioning fluid other fluids including sterile water or any other vaporizable liquid that is compatible with the body tissue may be used. In this example one mixes a vaporized liquid with the wash gas to generate a single phase wash gas, which is a gas that is free of liquids or substantially free of liquids, but a wash gas that is sufficiently humidified or conditioned to a water vapor saturated state or a near water vapor saturated state. By vaporizing a vaporizable liquid, for example, sterile water in the presence of the wash gas one inhibits or prevents liquid entrainment or atomization of liquid water droplets into the wash gas thus assuring that the wash gas, when conditioned, will remain in the gaseous state.

In the embodiment shown in FIG. 2 the gas conditioning housing 13 has an outside dimension sufficiently small that allows one to grasp the housing 13 and use the housing 13 as a handle for the nozzle 12 thus providing a dual function. The placement of the gas conditioning housing 13 in close proximity to the wash gas delivery tubing or blowpipe 11 allows one to use the gas conditioning housing 13 as a handle or grip for manipulating the blowpipe 11 to thereby enable one to direct the wash gas to the proper location at the surgical site. Blowpipe 11 may be made from rigid material or a bendable material, which retains its form once bent to allow the surgeon to position the nozzle 12 for the most effective delivery of wash gas to a surgical site.

Before the wash gas is ejected from nozzle 12 the wash gas may have to be heated as well as hydrated i.e. conditioned in the wash gas conditioning housing 13. Once the wash gas has been conditioned the wash gas, which is a single gaseous phase fluid stream, for example a single phase fluid stream of water vapor and gaseous carbon dioxide, can be directed at a surgical site to remove unwanted debris that may hinder a surgeons view of the surgical site and thus impede the medical procedure.

FIG. 2 shows an example of an interior of a gas conditioning housing 13. Located within gas conditioning housing 13 is an electrical heater assembly 37 for heating the wash gas to a temperature within a desired tissue friendly temperature range, which typically is about 35-40° C. That is, a single-phase wash gas can be heated as well as hydrated to increase the relative humidity of the wash gas to at or near 100% although in some applications other humidification levels may be selected. As described hereinafter one can use a source of vaporized liquid to hydrate the wash gas without atomization of the liquid and without the need to introduce a pressurized liquid stream into the single-phase surgical blower.

More specifically, FIG. 2 shows a cross sectional view of a multilayer media 39 comprising a plurality of three layers of materials 36, 37 and 38 which may be wound into a spiral configuration that may be inserted into a central chamber 40 in gas conditioning housing 13. In the spiral configuration state, as shown in FIG. 2, a hydrating liquid may be brought into proximity of a heater assembly 37 through an absorbing action of a hydrophilic layer 36 in media 39. The absorbing action of the hydrophilic layer 36 creates a source of stagnant hydrating liquid proximate the heater assembly 37 where the hydrating liquid can be vaporized. The vaporizable hydrating liquid is preferably a sterile saline solution, however sterile liquid water and other vaporizable liquids may be used without departing from the spirit and scope of the invention. A layer of porous netting 38 allows the wash gas to flow therethrough so the wash gas can be brought into proximity of the water vapor and the heater assembly 37 to enable the wash gas to be brought to a conditioned state through heating and hydration of the wash gas. In this example the vaporized liquid remains in a static, stagnant or non-flowing condition within the media 39 and the liquid, which is in the vapor phase, is absorbed by the wash gas as the wash gas flows through the stagnant source of water and water vapor located in hydrophilic layer 36. The present invention eliminates the need for having both a liquid stream and a gas stream since the presence of a stagnant source of water vapor in the chamber 40 in the gas conditioning housing allows the water vapor to freely intermix with the wash gas since both are in a gaseous state.

In order to secure the multilayer media 39 in the housing 13 the multilayer media 39 may be wound into a diameter slightly larger than the diameter of housing 13 to enable one to friction fit multilayer media 39 in housing 13. If frictional forces are used to hold multilayer media 39, then the multilayer media should be selected to offer sufficiently low flow resistance so that the wash gas flow flowing thereto will not displace the multilayer media 39.

Alternatively, multilayer media 39 could be adhesively secured to housing 13. It is noted that an advantage of the friction fit of multilayer media 39 in housing 13 is that the friction fit reduces the need for an adhesive to hold multilayer media 39 in place. An adhesive may interfere with the flow of wash gas from one layer of multilayer media 39 to another. An alternate method of holding the multilayer media 39 in position may be to use a radial support to support the downstream end of multilayer media 39. Other methods of securing the multilayer media 39 may also be used to maintain the multilayer media 39 in position to deliver hydrated wash gas to outlet port 13c.

To decrease the pressure drop through netting 38 two or more layers of netting may be placed proximate each other to increase the porosity through the netting. That is, netting 38 provides flow passages for the wash gas to flow from plenum chamber 31 to plenum chamber 32 without undue but sufficient resistance so that the hydration liquid and the wash gas can be maintained in proximity to enable hydration to take place. In some cases the netting 38 may be omitted.

Multilayer media 39 may include at least one layer of a liquid transfer media, which for example may be a hydrophilic media 36 that readily absorbs and retains a volume of hydration liquid, such as sterile water, provided to plenum chamber 31. As illustrated in FIG. 2 the plenum chamber 31 has an expanded flow area as opposed to the flow area in blow pipe 11. The expanded area in plenum chamber 31 reduces the velocity of the wash gas therein so that when the wash gas flows through the multilayer media 39 the wash gas lingers in the presence of the stagnant conditioning fluid, which is located in the hydrophilic media 36. That is the hydrating fluid/gas is introduced and held in the media hydrophilic media 36 so that fluid is stagnant or has no velocity. The slowing down of the wash gas by expansion of the flow area allows the wash gas to linger in the presence of the evaporating water from the stagnate source of conditioning fluid which allows the wash gas to be humidified by the evaporating conditioning fluid, which is in contrast to the entrainment and atomization of liquid particles that occurs when fast moving streams of gas and liquid flow past each other.

While other types of materials, for example wicking materials, may be used to deliver the hydration liquid, which is preferable a saline solution containing sterile water, into proximity of the heater assembly 37, the hydrophilic media 36 may bring the hydration liquid in close proximity to both heater assembly 37 and the wash gas through an absorbing action. Similarly, two or more layers of hydrophilic material may be used to bring the hydration liquid proximate the heater assembly.

In the example shown the multilayer media 39 may include a heater assembly 37, which may comprise an elongated flexible heating element that has external electrical leads 16a extending into electrical cord 16 for connecting the heater assembly to a source of electrical power. The heater assembly layer 37 may be thin and flexible such that when it is sandwiched between the hydrophilic layer 36 and the layer of netting 38 the combination can be wound into a spiral configuration that can be inserted within housing 13. An advantage of the spiraled configuration is that it provides a continuous extended area for heating and hydration of the wash gas, i.e., the wash gas flow path extends from side to side of housing 13. In the preferred embodiment, heater assembly 37, for example, is a resistance-heating element made of etched copper foil coated with a layer of polyimide. Another layer of polyimide may coat the foil surface. The coating of polyimide reduces the likelihood of heater assembly 37 from contacting the hydration liquid or hydrated wash gas such that an electrical short results. As discussed above, however, other types of heater and other types of absorbent material may be used with the invention.

One end of heater assembly 37 may terminate with a temperature sensor 35 for measuring the temperature of the wash gas in the plenum chamber 32. In other embodiments, multiple temperature sensors may be used and may be located elsewhere to either sense the temperature of the wash gas directly or sense the temperature of the heater. The temperature sensor can be located in the plenum chambers 32 or located in the blowpipe 11. In some cases, a remote sensor (e.g. an electronic infrared sensor) exterior to the blowpipe could be used. When heater assembly 37 is layered with the other materials of multilayer media 39 and friction fit into housing 13, temperature sensor 35, for example may be a thermistor that detects the temperature of the heater at lower plenum chamber 32. A heater control, not shown, can increase or decrease the power supplied to heater assembly 37 to maintain the temperature within a desirable range for injection into a body cavity. The opposite end of heater assembly 37 may terminate with electrical leads 14 which can be connected to a power source. When heater assembly 37 is layered with netting 38 and hydrophilic media 36 and assembled into a spiral configuration, electrical leads 16a may extend beyond the multilayer media 39. Thus, when the multilayer media 39 is placed in housing 13, the electrical leads 16a may extend beyond housing 13 for connection to a source of electrical power.

In the example shown, the gas conditioning housing 13 includes a temperature sensor 35 and a moisture sensor 40 and a remote control (not shown), which is connected through electrical cord 16 for maintaining the wash gas at a tissue friendly temperature.

While the above is an example of a gas conditioning housing for conditioning the wash gas by introducing water vapor into the wash gas other means and methods may be used to hydrate the wash gas prior to delivery of the wash gas to the surgical site.

In operation of the wash gas system shown in FIG. 1 and FIG. 2 one hydrates the wash gas through injection of a charge of hydration liquid, such as liquid water, which is injected into housing 13 through port 30 where the hydration liquid can be used to humidify the wash gas while a heater can bring the wash gas to a temperature near body temperature. In the cleaning of a surgical site the unconditioned wash gas enters inlet 13b and flows into plenum chamber 31. The wash gas then flows through the cylindrical member 39, which can both heat and hydrate the wash gas to condition the wash gas. The conditioned wash gas then flows into plenum chamber 32, which directs the wash gas past a temperature sensor 35. Temperature sensor 35 can be used to send a signal to a controller (not shown) where the temperature of the conditioned wash gas can be monitored and controlled. If the temperature of the wash gas is too low the temperature of the wash gas can be increased by supplying additional power to heater 37 through electrical cord 16. Similarly, if the temperature the gas is too high the power delivered to heater 37 can be decreased to lower the temperature of the wash gas. In the meantime the water in the hydrophilic media 36 vaporizes and is mixed with the wash gas and is carried with the wash gas into the plenum chamber 32. The above is an example of a gas conditioning housing 13 suitable for simultaneously heating and hydrating a wash gas to the proper temperature and humidity prior to using the wash gas to remove debris from a surgical site although other means and methods for conditioning the wash gas may be used.

The conditioned wash gas, which is both hydrated and heated is directed through outlet 13c into blowpipe 11 and eventually discharged in a single-phase stream, i.e. a gas stream through nozzle 12. A nozzle 12 is selected so as to divert the gas outward to the surgical site by maintaining an isothermal flow or substantial isothermal flow to prevent condensation or cooling of the wash gas to a temperature that may damage or harm the tissue at the surgical site. That is, the flow conditions should be selected so as the velocity of the wash gas is kept below a jet streaming velocity. While the wash gas has been both heated and hydrated in some cases the temperature of the incoming wash gas may be at a temperature where heating of the wash gas is unnecessary.

FIG. 3 shows the system of FIG. 1, which eliminates the need to recharge the hydrator in the gas conditioning housing during use of the single-phase wash system 10. In the example shown the port 14 of the gas conditioning housing 13 connects to a source of hydration fluid 54 through tubing 50. The hydration fluid 54, which is located in flexible pouch 53, is supported on a member 55 at a level above the gas conditioning housing 35 in order to provide a positive head of hydration fluid, which can be used to supply hydration fluid on-the-go. A valve 51, for example a drip valve, is located in fluid line 50 to control the egress of hydration fluid from pouch 53 into an internal chamber formed by curved tube 52 so as to prevent over saturation of the media in the gas conditioning housing 35. While the single-phase wash system 10 may be used with or without a continuous source of hydration fluid the connection to an external source of hydration fluid can eliminate the need to periodically recharge the media 39. A further advantage is that the other fluids can be introduced into the single-phase wash system 10 through the remote source.

As has been described the invention includes a method of enhancing visualization at a surgical site and particularly at an anastomosis site by removing unwanted debris and without generating unwanted debris at the anastomosis site during an on-the-go medical suturing procedure of a blood vessel and without desiccation of the blood vessel at the anastomosis site. In the process described one directs a wash gas into a wash gas conditioning housing 13 and conditions the wash gas by heating the wash gas to a tissue friendly temperature while increasing the relative humidity thereof by vaporizing a liquid in the presence of the wash gas. The proximate of the vaporized liquid proximate the wash gas allows for on-the-go mixing the vaporized liquid and the wash gas to form a single stream of wash gas. Once the wash gas is conditioned the operator can direct the conditioned single-phase wash gas through a nozzle 12 and onto the tissue at a surgical site to remove debris at the surgical site with assurance that the wash gas does not desiccate or harm the tissue at the surgical site. A benefit of heating and vaporizing the liquid is that vaporizing the liquid prevents formation of liquid droplets since the liquid goes directly from the liquid phase to the gas phase where the water vapor in the gas phase can be intermixed with the wash gas to hydrate the wash gas.

Thus the present invention comprises a single-phase surgical blower having a gas conditioning housing for hydrating a wash gas while inhibiting or preventing entrainment of liquid droplets therein and an outlet on the gas conditioning housing for directing a stream of conditioned wash gas at a dynamic surgical site to remove debris from the surgical site without adversely affecting the body tissue at the surgical site.

We claim:

1. A single-phase surgical blower for clearing unwanted debris from a surgical site during the anastomosis on coronary arteries while the heart continues to beat without generating additional debris and without desiccating tissue at the surgical site comprising:
    a source of a single-phase wash gas;
    a regulator for controlling a flow of the single-phase wash gas;
    a filter for removing unwanted particles from the wash gas;
    a nozzle for delivery of the single-phase wash gas to the surgical site, said nozzle diverting the single-phase was gas outward to maintain an isothermal flow of wash gas to the surgical site; and a wash gas conditioning housing located in fluid communication with the source of the wash gas, said wash gas conditioning housing including a heater for elevating a temperature of the wash gas to a tissue friendly level, a hydrophilic media and a stagnant source of vaporizable liquid located in a hydrophilic media where the vaporizable liquid and the wash gas linger as the vaporizable liquid evaporates and hydrates the wash gas while inhibiting or preventing entrainment of the vaporizable liquid into the wash gas to bring the wash gas to a conditioned gaseous single-phase state whereby directing a stream of the conditioned single phase wash gas at the surgical site blows away unwanted debris from the surgical site without liquid droplets desiccating tissue at the surgical site.

2. The single-phase surgical blower of claim 1 where the single-phase wash gas is carbon dioxide.

3. The single-phase surgical blower of claim 1 wherein the vaporizable liquid comprises a saline solution containing sterilized water.

4. The single-phase surgical blower of claim 1 including a single lumen bendable delivery tube in fluid communication with said housing and said nozzle.

5. The single-phase surgical blower of claim 1 wherein the surgical site is a dynamic surgical site, the wash gas is directed through an elongated bendable blowpipe and the nozzle at a distal end of the blowpipe.

6. A single-phase surgical blower for clearing an anastomosis site comprising:
a wash gas conditioning housing having a plenum chamber containing a hydrophilic member containing a stagnate source of water in a gaseous state within the hydrophilic member for hydrating a wash gas by allowing the wash gas and the water in the gaseous state to linger in the presence of each other to humidify the wash gas to form a single-phase conditioned wash gas while inhibiting or preventing entrainment of liquid droplets therein;
an inlet for connecting the wash gas conditioning housing to a source of a single-phase wash gas; and
a blowpipe in fluid communication with said gas conditioning housing for directing a stream of the single-phase conditioned wash gas outward to maintain an isothermal flow of the single-phase conditioned wash gas at a surgical site to remove debris from the surgical site without generating additional debris and without desiccating tissue at the surgical site.

7. The single-phase surgical blower of claim 6 including a regulator for controlling the flow of the single-phase conditioned wash gas through said blowpipe.

8. The single-phase surgical blower of claim 7 wherein the regulator for controlling the flow of the single-phase conditioned wash gas through said blowpipe is located upstream of the wash gas conditioning housing.

9. The single-phase surgical blower of claim 8 wherein the blowpipe is bendable.

10. The single-phase surgical blower of claim 9 including a nozzle on a terminal end of the blowpipe.

11. The single-phase surgical blower of claim 10 wherein the wash gas conditioning housing includes a heater, and the wash gas lingers proximate the stagnate source water in a gaseous state.

12. The single-phase surgical blower of claim 11 where the wash gas conditioning housing includes a temperature sensor and a moisture sensor for maintaining the wash gas at a tissue friendly temperature and a source of hydration fluid for delivery of hydration fluid on-the-go.

13. A method of on-the-go enhancing visualization at an anastomosis site as blood is pumped through arteries in a patient by removing unwanted debris and without generating unwanted debris at the anastomosis site during a medical suturing procedure of a blood vessel and without desiccation of the blood vessel at the anastomosis site comprising;
directing a single-phase wash gas into an inlet of a plenum chamber of a wash gas conditioning housing;
conditioning the single-phase wash gas by heating the single-phase wash gas in the plenum chamber to a tissue friendly temperature while increasing the relative humidity thereof by vaporizing a liquid in the presence of the wash gas and allowing the vaporized liquid and the wash gas to linger and mix in the presence of each other as the wash gas is humidified by the vaporized liquid to form a single conditioned wash gas stream;
directing the single conditioned wash gas stream to an outlet of the plenum chamber of the gas wash conditioning housing; and
blowing the single conditioned wash gas stream outward to maintain an isothermal flow of the wash gas at the anastomosis site to remove unwanted debris from the anastomosis site without adversely impacting body tissue at the anastomosis site.

14. The method of claim 13 including controlling the delivery of the single-phase wash gas by generating a voice command to change the rate of delivery of the single-phase wash gas to the anastomosis site.

15. The method of claim 13 including maintaining the temperature of the single-phase wash gas at about 35-40° C. and the relative humidity of the wash gas at or near a state of saturation.

16. The method of claim 13 including the step of inhibiting and preventing micro impacts of liquid droplets at the anastomosis site by maintaining the single-phase wash gas in a vapor phase after the single-phase wash gas has been discharged from a nozzle.

17. The method of claim 16 wherein the velocity of the single-phase wash gas is kept below a jet streaming velocity.

18. The method of claim 16 wherein the single-phase wash gas flows through the plenum chamber containing a stagnant source of water vapor to increase the humidity of the single-phase wash gas as the single-phase wash gas flows therethrough.

19. The method of claim 16 including allowing the single-phase wash gas to linger proximate the vaporized liquid to hydrate the single-phase wash gas without atomization of the vaporized liquid.

20. The method of claim 16 including the step of on-the-go supplying of the vaporized liquid to the wash gas conditioning housing.

21. The method of claim 13 including directing the single-phase wash gas through a nozzle to generate an isothermal expansion of the conditioned single-phase wash gas after the single-phase wash gas has been conditioned to prevent condensation of the water vapor in the wash gas.

* * * * *